United States Patent [19]
Hagiwara et al.
[11] Patent Number: 4,751,163
[45] Date of Patent: Jun. 14, 1988

[54] 1,1,4,4-TETRAPHENYL-1,3-BUTADIENE DERIVATIVE AND ELECTROPHOTOGRAPHIC LIGHT-SENSITIVE MATERIAL USING THE SAME

[75] Inventors: Toshimitsu Hagiwara; Haruki Tsuruta, both of Tokyo, Japan

[73] Assignee: Takasago Perfumery Co., Ltd., Tokyo, Japan

[21] Appl. No.: 58,724

[22] Filed: Jun. 5, 1987

[30] Foreign Application Priority Data

Jun. 5, 1986 [JP] Japan ............................... 61-131000

[51] Int. Cl.⁴ ...................... G03G 5/14; C07D 239/02
[52] U.S. Cl. ...................................... 430/59; 546/315; 546/330
[58] Field of Search ................... 430/59; 564/315, 330

[56] References Cited

U.S. PATENT DOCUMENTS

| | | | |
|---|---|---|---|
| 3,906,399 | 9/1975 | Dienes et al. | 252/301.17 X |
| 4,045,220 | 8/1977 | Contois et al. | 430/83 X |
| 4,105,447 | 8/1978 | Fox | 430/83 X |
| 4,145,214 | 3/1979 | Yoerger | 430/71 |
| 4,195,990 | 4/1980 | Standenmayer et al. | 430/83 X |
| 4,250,053 | 2/1981 | Smith | 430/281 X |

FOREIGN PATENT DOCUMENTS

| | | |
|---|---|---|
| 1329581 | 9/1979 | United Kingdom . |
| 2121789 | 1/1984 | United Kingdom . |
| 2151033 | 7/1985 | United Kingdom . |

OTHER PUBLICATIONS

C. E. H. Bawn, "Oxidation by a Cation Radical: Electron Transfer from 1,1-bis-(dimethylaminophenyl) ethylene", Chemical Comm., 1, pp. 599-600, (1968).

*Primary Examiner*—Roland E. Martin
*Attorney, Agent, or Firm*—Sughrue, Mion, Zinn, Macpeak & Seas

[57] ABSTRACT

A 1,1,4,4-tetraphenyl-1,3-butadiene derivatives represented by formula (I):

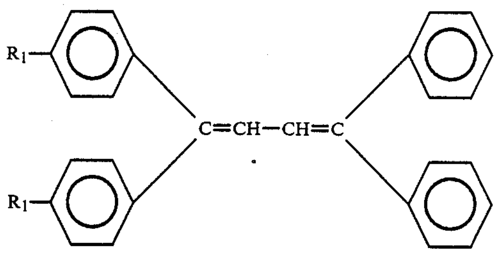

(I)

wherein $R_1$ represents a di-lower alkylamino group, and $R_2$ represents a hydrogen atom or a di-lower alkylamino group, is disclosed, which has useful characteristics such as excellent static charge retention ability. An electrophotographic light-sensitive material using the foregoing derivative can satisfy the requirements, e.g., for high sensitivity, low residual potential, less light fatigue even after repeated use, and excellent durability.

8 Claims, 2 Drawing Sheets

1,1,4,4-TETRAPHENYL-1,3-BUTADIENE DERIVATIVE AND ELECTROPHOTOGRAPHIC LIGHT-SENSITIVE MATERIAL USING THE SAME

FIELD OF THE INVENTION

This invention relates to a 1,1,4,4-tetraphenyl-1,3-butadiene derivative that functions effectively as a charge transporting substance in an electrophotographic light-sensitive material in the system of using a charge generating substance and a charge transporting substance and is represented by formula (I):

(I)

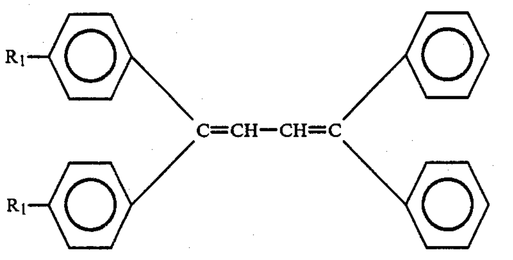

wherein $R_1$ represents a di-lower alkylamino group, and $R_2$ represents a hydrogen atom or a di-lower alkylamino group, and to an electrophotographic light-sensitive material using the same.

BACKGROUND OF THE INVENTION

In electrophotographic light-sensitive materials widely used in recent years, there are used selenium, cadmium sulfide, zinc oxide, and the like as inorganic photoconductive substances; and various photoconductive polymers including poly-N-vinyl carbazole and polyvinyl anthrathene as organic photoconductive substances. However, these substances are not satisfactory in film-forming properties and flexibility and have drawbacks that they likely cause cracks or exfoliation when left in the film state. In order to compensate these drawbacks, it has been proposed to add a plasticizer or a binder, but electrophotographic properties such as sensitivity or residual potential are reduced though the flexibility is improved and, accordingly, it has been extremely difficult to obtain a practically useful light-sensitive material. Low-molecular weight organic photoconductive compounds have themselves no film-forming ability but can be formed into films capable of providing light-sensitive materials excellent in film-forming properties and flexibility by appropriately combining with a high-molecular weight binder such as polyester resins, polyvinyl chloride resins, and polycarbonate resins.

In addition to the system of using these photoconductive substances, there are proposed various methods of obtaining two functions of the photoconductive substance, that is, generation of charge carriers and transportation of generated charges, by separate organic compounds as described in, for example, U.S. Pat. No. 3,791,826. In this method, it is possible to obtain electrophotographic light-sensitive materials having high sensitivity by the combination of substances having a high generation efficiency for charge carriers with substances having a high charge transporting ability. However, it is not always possible to simultaneously attain those various properties required for the electrophotographic light-sensitive material, that is, high surface charge, high charge retention ability, and high photosensitivity, with substantially no residual potential. In order to obtain practically useful light-sensitive materials having such various properties, it is important to provide high generation efficiency of charge carriers in the charge generating substance and rapid transportation of charge carriers in the charge transporting substance, as well as efficient injection of electric charges from the charge generating substance to the charge transporting substance, i.e., efficient injection of charge carriers from the charge generation layer to the charge transport layer in the laminate-type light-sensitive material. Although it has been attempted to explain the injection efficiency by means of a correlationship with the ionization potential of the charge transporting substance, it still lacks in generality, and explanation cannot be made systematically for the entire charge transporting substance. The charge injection varies depending on the characteristics of the interface between the charge generating substance (or charge generation layer) and the charge transporting substance (or charge transport layer) and is not uniform among various kinds of substances.

On the other hand, while several compounds have already been known from 1,1,4,4-tetraphenyl-1,3-butadiene derivatives with which this invention is concerned, only 1,1,4,4-tetraphenyl-1,3-butadiene is known to be useful as the electrophotographic light-sensitive material (as described in, for example, M. Kleinerman et al., *J. Chem. Phys.*, 37, 1825 (1962) and Japanese Patent Application (OPI) No. 24248/77). (The term "OPI" as used herein refers to a "published unexamined Japanese patent application".) However, 1,1,4,4-tetraphenyl-1,3-butadiene and known alkyl-, alkoxy-, or halogen-substituted 1,1,4,4-tetraphenyl-1,3-butadiene derivatives thereof are extremely of low sensitivity and poor in solubility in binder polymers. Further, although only 1,1,4,4-tetrakis(p-dimethylaminophenyl)-1,3-butadiene has been known so far as alkylamino group-containing derivatives (as described in C. E. H. Bawn et al, *Chem. Commun.*, 599 (1968)), this compound has no electrostatic charge retention ability and cannot substantially be used as the light-sensitive material.

In electrophotographic light-sensitive materials having function-separated type light-sensitive layers, though high sensitivity can possibly be obtained by selection and combination of substances having respective functions as described above, the conventional electrophotographic light-sensitive materials of this type have a drawback that when used repeatedly according to the electrophotographic process, the ability to recover original charging properties is reduced or the light sensitivity is decreased to thereby shorten the life time of the light-sensitive material. That is, when the actual process of electrophotography such as charging, exposure, and cleaning is repeated for many times, one or more of light-fatigue phenomena are brought about such as fluctuation of the surface charge after charging, reduction in charge retention ability, reduction in light sensitivity, increase in residual potential, and the like, which greatly reduce the performance of electrophotography and bring about a severe problem for practical use.

The present inventors have made extensive investigations to various compounds which are suitable for the preparation of an electrophotographic light-sensitive material of a further higher performance among 1,1,4,4-tetraphenyl-1,3-butadiene derivatives having one or two di-lower alkylamino groups unexpectedly possess excellent properties as an electrophotographic light-sensitive material, that is, satisfactory solubility, high sensitivity with low residual potential, and high durability with less light fatigue even after repeated use, which finding lead to this invention.

SUMMARY OF THE INVENTION

An object of this invention is to provide a 1,1,4,4-tetraphenyl-1,3-butadiene derivative represented by formula (I):

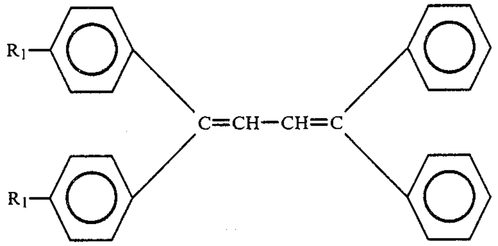
(I)

wherein $R_1$ represents a di-lower alkylamino group, and $R_2$ represents a hydrogen atom or a di-lower alkylamino group.

Another object of this invention is to provide an electrophotographic light-sensitive material containing such a derivative as a charge transporting substance.

BRIEF DESCRIPTION OF THE ACCOMPANYING DRAWINGS

FIG. 1 is an explanatory cross-sectional view illustrating one embodiment of the electrophotographic light-sensitive material according to this invention; and FIG. 2 is a chart representing the result of Example 9 tested for the endurance of a light-sensitive material using exemplified Compound (7): 1,1-bis(p-diethylaminophenyl)-4,4-diphenyl-1,3-butadiene synthesized in Example 5 of this invention.

DETAILED DESCRIPTION OF THE INVENTION

Figure 1:
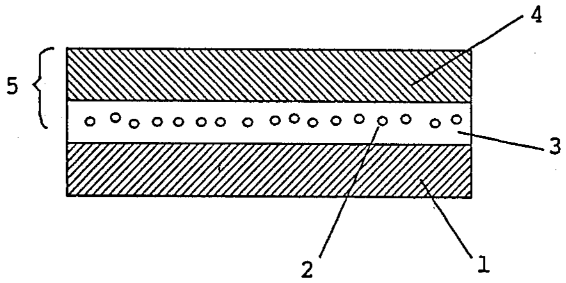

The term "alkyl group" in the di-lower alkylamino group for $R_1$ or $R_2$ in formula (I) means a straight or branched chain alkyl group containing from 1 to 4 carbon atoms. Specific examples of the alkyl group include a methyl group, an ethyl group, an n-propyl group, an isopropyl group, an n-butyl group, an isobutyl group, and a sec-butyl group.

A 1,1,4,4-tetraphenyl-1,3-butadiene of formula (I) according to this invention can be prepared derivative of the following procedures:

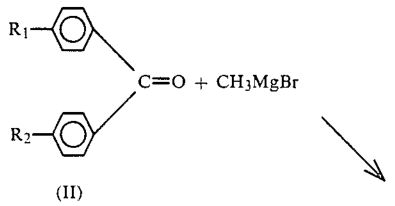
(II)

-continued

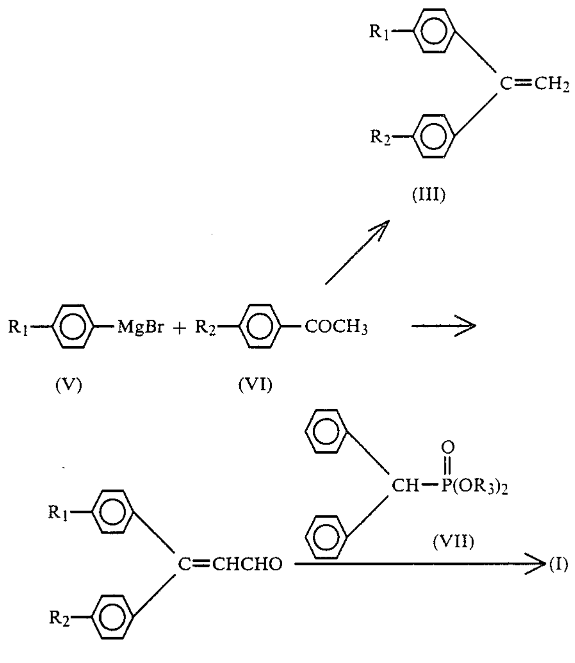
(III)
(V) (VI)
(VII)
(IV)

wherein $R_3$ represents a lower alkyl group, and $R_1$ and $R_2$ have the same meanings as described above.

At first, aniline is reacted with a tri-lower alkyl phosphate through a known reaction to obtain a di-lower alkylaniline which is further reacted with phosgene to obtain a di-lower alkylamino group-substituted benzophenone (II). After reacting the benzophenone derivative (II) with a Grignard reagent prepared from methyl bromide and magnesium, the reaction mixture is treated with a saturated aqueous ammonium chloride solution to obtain a 1,1-diphenylethylene derivative (III). On the other hand, the 1,1-diphenylethylene derivative (III) can also be synthesized by reacting acetophenone or an acetophenone derivative (VI) obtained by lower alkylation of 4-aminoacetophenone through a known reaction, with a Grignard reagent (V) prepared from a 4-di-lower alkylaminophenyl bromide obtained through bromination of a di-lower alkylaniline and magnesium, and then treating with a saturated aqueous ammonium chloride solution. Thereafter, by reacting the 1,1-diphenylethylene derivative (III) with a Vilsmeier reagent prepared from dimethylformamide and phosphorus oxychloride in accordance with the method of H. Lovenz et al, *Helv. Chim. Acta,* 28, 600–612 (1945), there can be readily obtained a 3,3-diphenylacrolein derivative (IV).

Then, the 1,1,4,4-tetraphenyl-1,3-butadiene derivative (I) according to this invention can be obtained by reacting the thus obtained 3,3-diphenylacrolein derivative (IV) with an equimolar amount or slightly excess amount of a dialkyl 1,1-diphenylmethylphosphonate represented by formula (VII).

The alkyl group of the dialkyl 1,1-diphenylmethylphosphonate (VII) used herein is a lower alkyl group. The reaction of the acrolein compound (IV) and the phosphonate compound (VII) is conducted in the presence of a basic catalyst at a temperature of from room temperature to about 80° C. Examples of the basic catalyst used include sodium hydride, sodium amide, and alcoholates such as sodium methylate and sodium t-butoxide. Examples of solvents usable herein are lower alcohols such as methanol and ethanol; ethers such as 1,2-dimethoxyethane, diethyl ether, tetrahydrofuran, and dioxane; hydrocarbons such as toluene and xylene; and aprotic polar solvents such as dimethyl sulfoxide, N,N-dimethylformamide, and N-methylpyrrolidone.

Typical examples of 1,1,4,4-tetraphenyl-1,3-butadiene derivatives represented by formula (I) are listed below:

(1)

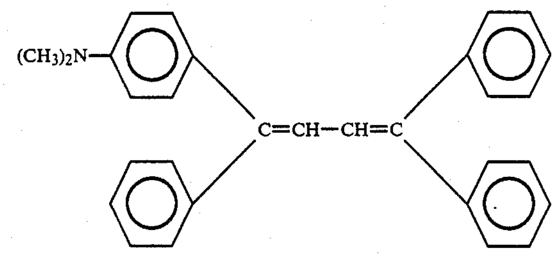

(2)

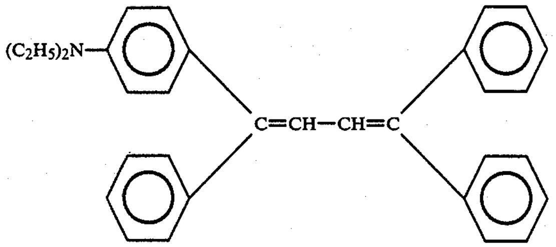

(3)

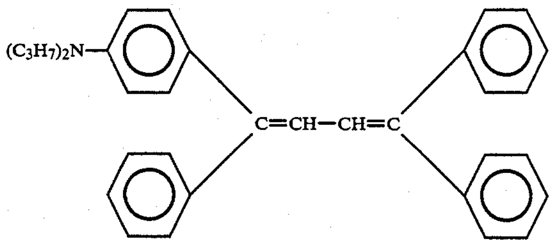

(4)

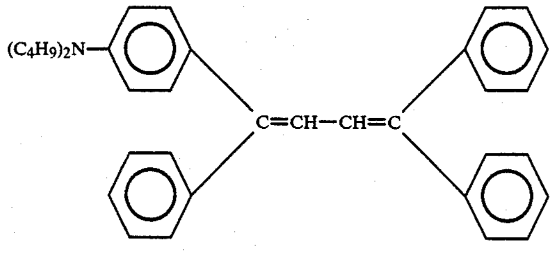

(5)

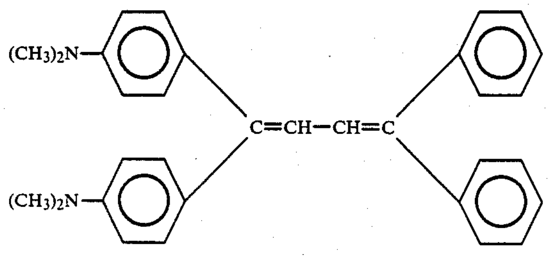

-continued (6)

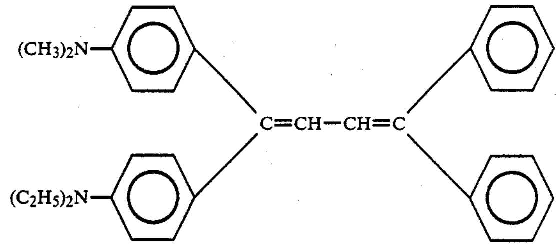

(7)

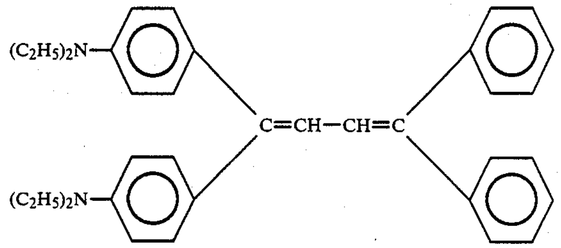

(8)

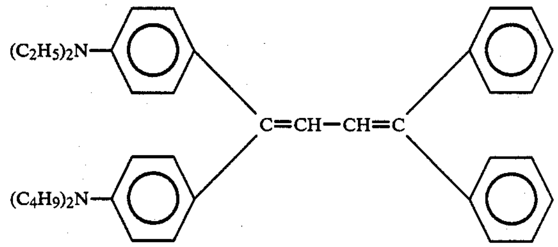

(9)

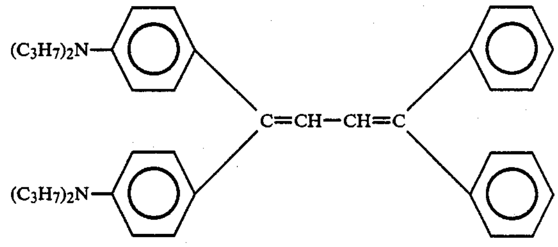

(10)

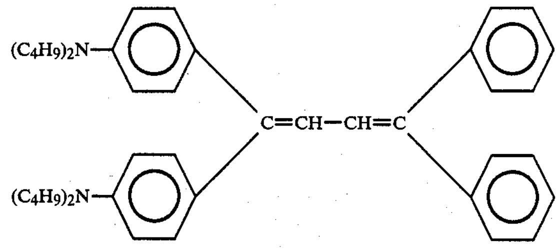

Among them, Compounds (2) and (7) are especially preferred.

The compound (I) according to this invention obtained as described above has excellent properties as a charge transporting substance in an electrophotographic light-sensitive material in which the charge generating substance and charge transporting substance are composed of different substances from each other.

Explanation will be made to an electrophotographic light-sensitive material using the compound according to this invention while referring to specific examples.

Electrophotographic light-sensitive material according to this invention is formed, for example, as shown in FIG. 1, wherein a light-sensitive material according to this invention is formed, for example, as shown in FIG. 1, wherein a light-sensitive layer 5 comprising a charge generation layer 3 mainly composed of a charge generating substance 2 and a charge transport layer 4 uniformly containing the compound (I) according to this invention is disposed on a conductive support 1.

That is, in the light-sensitive material according to this invention, a light which has transmitted through the charge transport layer 4 reaches the charge generating substance 2 dispersed in the charge generation layer 3 to cause electric charges, and the charge transport layer 4 accepts injection of charges to thereby effect the transportation thereof.

The light-sensitive material shown in FIG. 1 is prepared by (1) vacuum-depositing the charge generating substance 2, (2) coating a dispersion obtained by mixing and dispersing fine particles of the charge generating substance 2 with a binder, if required, or (3) coating a solution of the charge generating substance 2 dissolved in an appropriate solvent, on the conductive support 1 to form the charge generation layer 3; after drying, if further required, applying surface finishing by, for example, buff grinding or the like to adjust the layer thickness; and then, coating a solution containing the compound (I) according to this invention and the binder on the charge generation layer 3, followed by drying to form the charge transport layer 4. The coating is carried out by using ordinary means such as, for example, a doctor blade or a wire bar.

The thickness of the charge generation layer is not more than 5 μm, preferably not more than 2 μm, while the thickness of the charge transport layer is from 3 to 50 μm, preferably from 5 to 20 μm. The compound (I) according to this invention is blended into the charge transport layer at a ratio from 10 to 90% by weight, preferably from 30 to 70% by weight.

Examples of the conductive support usable herein include plates or foils of metals such as aluminum, plastic films vapor-deposited with a metal such as aluminum, or paper sheets applied with electrifying treatment.

Examples of the binder usable herein include polyester resins, polyvinyl chloride resins, acrylic resins, methacrylic resins, polystyrene resins, and polycarbonate resins. Among them, polyester resins and polycarbonate resins are preferred.

Examples of the charge generating substance include inorganic materials such as selenium and cadmium sulfide; and organic materials such as azo pigments (such as CI Pigment Blue 25 (color index: CI21180), CI Pigment Red 41 (CI21200), CI Acid Red 52 (CI45100), and CI Basic Red 3(CI45210)), phthalocyanine pigments (such as CI Pigment Blue 16 (CI74100)), indigo pigments (such as CI Vat Brown 5 (CI73410) and CI Vat Dye (CI73030)), perylene pigments (such as Algol Scarlet R (manufactured by Bayer AG), Indanthrene Scarlet R (manufactured by Bayer AG)); and further, Chlorodian-blue (that is, 4,4′-[(3,3′-dichloro-4,4′-biphenylylene)-bis(azo)]-bis-(3-hydroxy-2-naphthalinide)), methyl squarylium (that is, 2,4-bis-(2-methyl-4-dimethylaminophenyl)-1,3-cyclobutadienediylium-1,3-diolate), and hydroxy squarylium (that is, 2,4-bis-(2-hydroxy-4-dimethylaminophenyl)-1,3-cyclobutadienediylium-1,3-diolate).

The light-sensitive material according to this invention obtained as described above has excellent characteristics such as extremely high sensitivity, high flexibility, no characteristic changes due to charging and exposure, high durability, etc.

When the light-sensitive material according to this invention was charged by using a commercially available electrophotographic copying machine, exposed to light through an original to form electrostatic latent images, and developed by a developer, followed transferring the thus obtained toner images to common paper and then fixing the transferred images, clear copy images can be obtained exactly corresponding to the original.

This invention will now be described more specifically referring to the following Examples and Comparative Examples.

EXAMPLE 1

Synthesis of 1-(p-diethylaminophenyl)-1,4,4-triphenyl-1,3-butadiene (Exemplified Compound (2))

(1) Synthesis of 1-(p-diethylaminophenyl)-1-phenylethylene

After adding dropwise 100 ml of a benzene solution containing 8 g of acetophenone to a tetrahydrofuran solution of 4-diethylaminophenylmagnesium bromide prepared from 2 g of magnesium, 16 g of 4-bromodiethylaniline, and 100 ml of tetrahydrofuran, stirring was continued under reflux for 5 hours. After cooling, 200 ml of a saturated aqueous ammonium chloride solution was added thereto. The mixture was subjected to hydrolysis, and an organic layer was separated and washed with water. After distilling off the solvent, the residue was dissolved in benzene, and the solution was stirred and refluxed with the addition of 0.1 g of p-toluenesulfonic acid for one hour. After distilling off the solvent, the residue was dissolved in benzene, and the product was separated and purified by silica gel column chromatography.

(2) Synthesis of 3-(p-diethylaminophenyl)-3-phenylacrolein

After adding dropwise 3.9 g of phosphorus oxychloride to a solution of 2.2 g of dimethylformamide (DMF) and 50 ml of 1,2-dichloroethane at from 0° to 5° C., the mixture was stirred at that temperature for 30 minutes. Then, a solution of 5.2 g of 1-(p-diethylaminophenyl)-1-phenylethylene in 50 ml of 1,2-dichloroethane solution was added dropwise thereto at that temperature over 30 minutes, and the mixture was reacted from 5 hours at room temperature. Hydrolysis was conducted with an addition of 100 cc of water containing 10 g of sodium acetate. After separating and water-washing an organic layer, the solvent was distilled off to obtain 4.8 g of an oily substance which was subsequently separated and purified on silica gel column chromatography to obtain 3.3 g (yield: 57% (theory)) of an oily product.

Infrared absorption spectrum (Neat): $\nu(cm^{-1})$: 2980, 1655, 1605, 1568, 1520, 1410, 1348, 1250, 1203, 1128, 822, 715.

NMR spectrum (90 MHz, $CDCl_3$) δ ppm: 1.08 and 1.10 (6H, t, J=7.0 Hz); 3.40 and 3.41 (4H, q, J=7.0 Hz); 6.16–6.64 (3H, m); 7.14–7.25 (7H, m); 9.34 and 9.61 (1H, d, J=8.2 Hz).

(3) Synthesis of 1-(p-diethylaminophenyl)-1,4,4-triphenyl-1,3-butadiene 2.79 g of 3-(p-diethylaminophenyl)-3-phenylacrolein and 3.34 g of diethyl diphenylmethylphosphonate were dissolved in 100 ml of DMF, and 1.23 g of potassium t-butoxide was added thereto at room temperature. The temperature of the reaction mixture was increased to 31° C. by a heat generated and, thereafter, the reaction was conducted at room temperature for 4 hours. The reaction mixture was poured into 100 cc of ice water and stirred. Deposited crystals were collected by filtration, dissolved in benzene, and separated and purified on silica gel column chromatography. After distilling off benzene from the eluate, the purified product was recrystallized from ethyl acetate to obtain 2.9 g (yield: 68% (theory)) of a pale-yellow crystal. m.p.: 124°-5° C.

Infrared absorption spectrum (KBr): $\nu$(cm$^{-1}$): 3040, 2980, 1602, 1520, 1495, 1270, 1202, 750, 700, 610.

NMR spectrum (400 MHz, $CDCl_3$) $\delta$ ppm: 1.12 and 1.24 (6H, t, J=7.0 Hz); 3.31 and 3.71 (4H, q, J=7.0 Hz); 6.52 (1H, d, J=9.0 Hz); 6.71 (1H, m); 6.99-7.40 (19H, m).

EXAMPLE 2

Synthesis of 1,1-bis(p-dimethylaminophenyl)-4,4-diphenyl-1,3-butadiene (Exemplified Compound (5))

(1) Synthesis of 1,1-bis(4'-dimethylaminophenyl)ethylene

After adding 100 ml of benzene to a diethyl ether solution of methylmagnesium iodide prepared from 1.7 g of magnesium, 9.9 g of methyl iodide, and 100 ml of diethyl ether, 16.6 of 4,4'-bis-dimethylaminobenzophenone was gradually added thereto. After stirring at room temperature for 10 hours, the reaction mixture was decomposed by a saturated aqueous ammonium chloride solution, followed by stirring as it was for 2 hours. After separating and water-washing an organic layer, the solvent was distilled off, and the residue was recrystallized from ethanol to obtain 10.7 g of 1,1-bis(4'-dimethylaminophenyl)ethylene. The melting point was 121° to 122° C., and the theoretical yield was 65%.

(2) Synthesis of 3,3-bis(p-dimethylaminophenyl)acrolein

From 13.3 g of 1,1-bis(4'-dimethylaminophenyl)ethylene obtained in (1) above, 12.0 g (yield: 81% (theory) of 3,3-bis(p-dimethylaminophenyl)acrolein was obtained in the same procedures as in Example 1-(2). m.p.: 173° C.

Infraded abosrption spectrum (KBr): $\nu$(cm$^{-}$): 2900, 2810, 1645, 1605, 1565, 1520, 1365, 1195, 1138, 820.

NMR spectrum $\delta$ ppm: 3.01 and 3.03 (6H, s); 6.41 and 6.43 (1H, s); 6.66 and 6.71 (4H, dd, J=2.0, 6.9 Hz); 7.21 and 7.30 (4H, dd, J=2.0, 6.9 Hz); 9.45 and 9.48 (1H, s).

(3) Synthesis of 1,1-bis(p-dimethylaminophenyl)-4,4-diphenyl-1,3-butadiene 2.94 g of 3,3-bis(p-dimethylaminophenyl)acrolein obtained in (2) above and 3.34 g of diethyl diphenylmethylphosphonate were dissolved in 100 ml of DMF, and 0.6 g of sodium methylate was added thereto, followed by stirring for 4 hours. 3.5 g (yield: 79% (theory)) of a yellow crystal was obtained in the same procedures as in Example 1-(3). m.p.: 184°-5° C.

Infrared absorption spectrum (KBr): $\nu$(cm$^{-1}$): 3020, 2880, 2800, 1605, 1580, 1512, 1485, 1440, 1360, 1190, 1165, 950, 815, 762, 703, 692.

NMR spectrum (400 MHz, $CDCl_3$) $\delta$ ppm: 2.92 and 3.00 (12H, s (each)); 6.57-6.60 (3H, m); 6.74 (2H, dd, J=6.7, 2.1 Hz); 6.90 (1H, d, J=11.3 Hz); 7.10 (2H, dd, J=6.7, 2.1 Hz); 7.17-7.23 (7H, m); 7.31-7.38 (5H, m).

EXAMPLE 3

After mixing 0.2 g of Chlorodian-blue with 4 g of a dichloroethane solution containing 5% of a polycarbonate resin ("Jupilon S-2000", manufactured by Mitsubishi Gas Chemical Co., Ltd.), 20 ml of dichloroethane was added thereto, and the mixture was pulverized to not more than 1 μm by using a vibration mill to prepare a dispersion of charge generating pigment. The thus prepared dispersion was coated on an aluminum-deposited polyester film by using a wire bar and dried at 45° C. to prepare a charge generation layer of about 1 μm in thickness.

On the other hand, 0.1 g of exemplified Compound (2) was dissolved in 2 g of a dichloroethane solution containing 5% of the above-described polycarbonate resin to prepare a charge transport layer-forming solution. This solution was coated on the charge generation layer as prepared above to a dry film thickness of about 15 μm by using a doctor blade and dried at 45° C. to prepare a light-sensitive material. Electrophotographic properties were measured for the thus prepared light-sensitive material by using an electrostatic paper analyzer (mode SP-428, manufactured by Kawaguchi Denki Seisakusho) in a static method. That is, after applying corona discharge to the light-sensitive material at −6 kV, the surface potential Vo (unit: minus volt) was measured. Then, the material was placed in a dark place for 5 seconds, light at 5 lux was illuminated from a tungsten lamp to determine the exposure amount required for decaying the surface potential to one-half, that is, the half decay exposure E1/2 (lux.sec) and the surface residual potential $V_R$ (volt) after 20 seconds illumination of 5 lux-light. The results are shown in Table 1.

EXAMPLE 4

A light-sensitive material was prepared in the same manner as in Example 3 except for using exemplified Compound (5), and the performance as a light-sensitive material was examined. The results are shown in Table 1.

EXAMPLE 5

Exemplified Compound (7) was obtained in the same manner as in Example 2 except for using 4,4'-bis(p-diethylamino)benzophenone obtained by reacting diethylaniline with phosgene in the same manner as in Example 2, and a light-sensitive material was prepared in the same manner as in Example 3. Then, the performance as a light-sensitive material was examined. The results are shown in Table 1.

COMPARATIVE EXAMPLE 1

1,1,4,4-Tetraphenyl-1,3-butadiene (Comparative Compound (1)) was synthesized by the method of K. Takagi, et al., *Bull. Chem. Soc. Jpn.*, 57, 1887 (1984) and the method of W. Todros, *J. Chem. Soc.*, 1954, 2966.

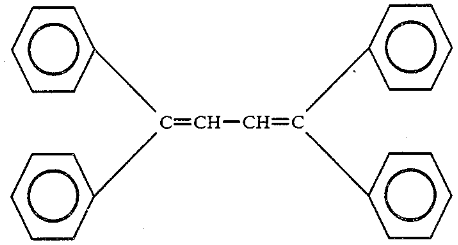

Comparative Compound (1) m.p.: 199° C.

A light-sensitive material was prepared in the same manner as in Example 3 except for using Comparative Compound (1) instead of exemplified Compound (2) used in Example 3. The thus obtained light-sensitive material was cloudy in which Comparative Compound (1) was deposited on the entire surface of the material, and the performance as a light-sensitive material was examined. The results are shown in Table 1.

COMPARATIVE EXAMPLE 2

1,1,4,4-Tetrakis(p-methoxyphenyl)-1,3-butadiene (Comparative Compound (2)) was synthesized by the method of Comparative Example 1. While this comparative compound had been intended to be dissolved in a dichloroethane solution containing a polycarbonate resin in the same manner as in Example 3, it was not dissolved therein, failing to prepare a light-sensitive material.

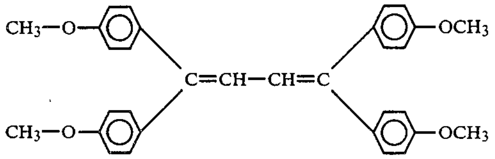

Comparative Compound (2) m.p.: 205° C.

EXAMPLES 6, 7 AND 8

Light-sensitive materials were prepared by using exemplified Compounds (2), (5), and (7), respectively in the same manner as in Example 3 except for replacing the Chlorodian-blue with phthalocyanine (τ-type phthalocyanine, manufactured by Toyo Ink Mfg. Co., Ltd.). The results are shown in Table 1.

COMPARATIVE EXAMPLE 3

A light-sensitive material was prepared using 1,1,4,4-tetrakis(p-dimethylaminophenyl)-1,3-butadiene (Comparative Compound (3)) synthesized by the method of C. E. H. Baun et al, *Chem. Commun.*, 599 (1968), and the performance as a light-sensitive material was examined. The results are shown in Table 1.

TABLE 1

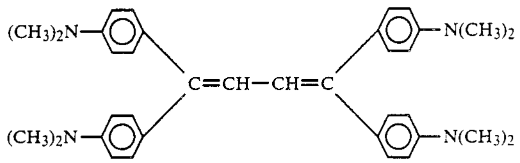

Comparative Compound (3) m.p.: 187° C.

| Example No. | Exemplified Compound used and Melting Point | $V_0$ (Volt) | E1/2 (Lux. sec) | $V_R$ (Volt) |
|---|---|---|---|---|
| 3 | (2) 124-125° C. | 500 | 3.8 | 5 |
| 4 | (5) 184-185° C. | 500 | 2.5 | 3 |
| 5 | (7) 167-168° C. | 450 | 2.0 | 0 |
| 6 | (2) 124-125° C. | 790 | 1.4 | 3 |
| 7 | (5) 184-185° C. | 580 | 1.2 | 0 |
| 8 | (7) 167-168° C. | 770 | 1.2 | 0 |
| Comparative Example 1 | Comparative Compound (1) 199° C. | 1180 | — | 900 |
| Comparative Example 3 | Comparative Compound (3) 187° C. | not charged | — | — |

As is apparent from Table 1, it can be seen that the light-sensitive materials of Examples 3, 4, 5, 6, 7, and 8 have excellent properties that cannot be found in the light-sensitive materials in Comparative Examples 1 and 3, such as surface potential ($V_o$) of from 450 to 770 V, half-decay exposure (E1/2) of from 1.2 to 3.8 lux.sec., and surface residual potential ($V_R$) of from 0 to 5 V.

EXAMPLE 9

Figure 2:
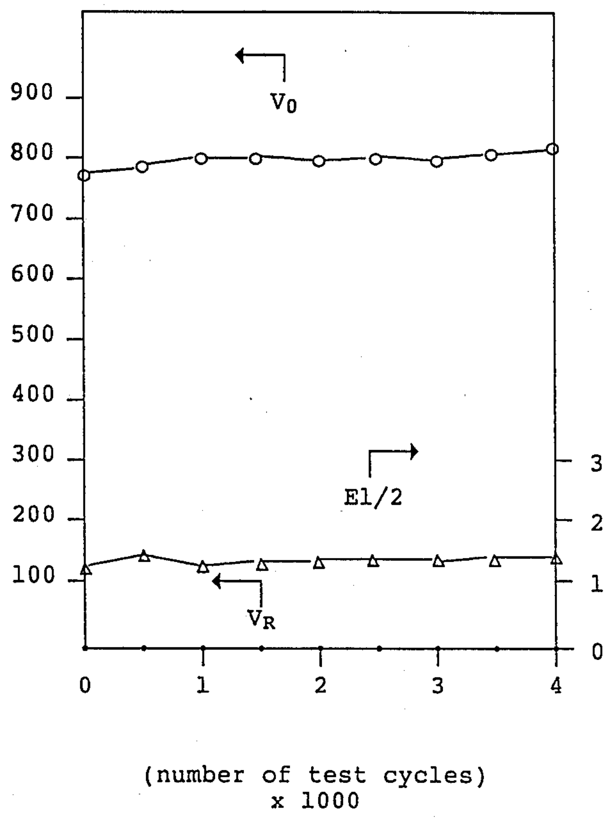

The light-sensitive material obtained in Example 8 was further illuminated with light at 10,000 lux for 3 seconds to eliminate the residual charges. Then, the material was again charged by applying corona discharge at −6 kV for 5 seconds, and the surface potential ($V_o$) was measured. After maintaining the material in a dark place for 5 seconds, the 5 lux-light was illuminated from a tungsten lamp to determine the half-decay exposure (E1/2) and the residual potential ($V_R$). Results obtained by repeating the test cycles are shown in FIG. 2. As is apparent from FIG. 2, the light-sensitive material according to this invention exhibits excellent durability for charged potential, sensitivity, and residual potential.

The present invention provides a novel 1,1,4,4-tetraphenyl-1,3-butadiene derivative which shows useful properties for an electrophotographic light-sensitive material, such as excellent electrostatic charge retention ability. In addition, the electrophotographic light-sensitive material using the compound according to this invention has characteristics that are highly required in the field of electrophotographic processes such as high sensitivity, low residual potential, less light fatigue after repeated use, and excellent durability and, thus, provides great industrial advantages.

While the invention has been described in detail and with reference to specific embodiments thereof, it will be apparent to one skilled in the art that various changes and modifications can be made therein without departing from the spirit and scope thereof.

What is claimed is:

1. An electrophotographic light-sensitive material having a charge generation layer and a charge transport layer on a conductive support, wherein said charge transport layer contains a 1,1,4,4-tetraphenyl-1,3-butadiene derivative represented by formula (I):

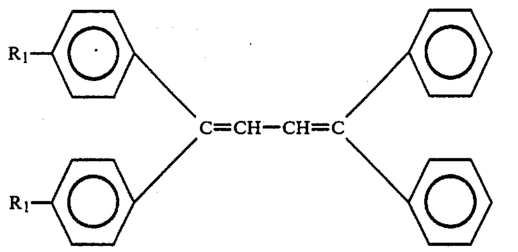

(I)

wherein $R_1$ is a di-lower alkylamino group, and $R_2$ is a hydrogen atom or a di-lower alkylamino group.

2. An electrophotographic light-sensitive material as in claim 1, wherein the alkyl group in the di-lower alkylamino group for $R_1$ or $R_2$ in formula (I) is a straight or branched chain alkyl group containing from 1 to 4 carbon atoms.

3. An electrophotographic light-sensitive material as in claim 2, wherein the compound of formula (I) is represented as follows:

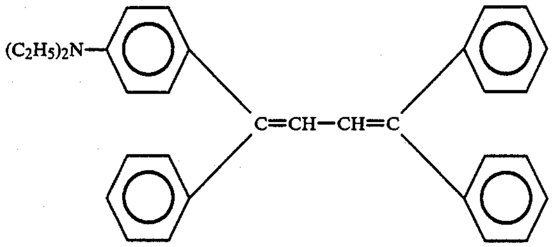

4. An electrophotographic light-sensitive material as in claim 2, wherein the compound of formula (I) is represented as follows:

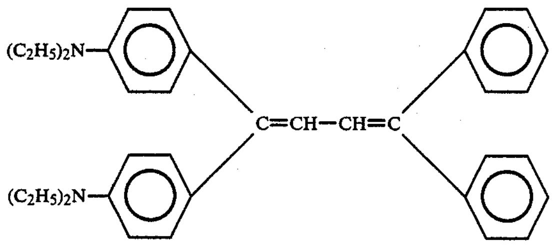

5. A 1,1,4,4-tetraphenyl-1,3-butadiene derivative represented by formula (I):

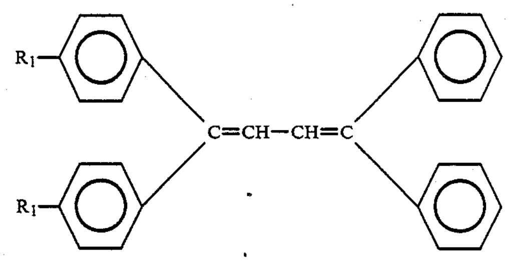

(I)

wherein $R_1$ is a di-lower alkylamino group, and $R_2$ is a hydrogen atom or a di-lower alkylamino group.

6. A 1,1,4,4-tetraphenyl-1,3-butadiene derivative as in claim 5, wherein the alkyl group in the di-lower alkylamino group for $R_1$ or $R_2$ in formula (I) is a straight or branched chain alkyl group containing from 1 to 4 carbon atoms.

7. A 1,1,4,4-tetraphenyl-1,3-butadiene derivative as in claim 6, wherein the compound of formula (I) is represented as follows:

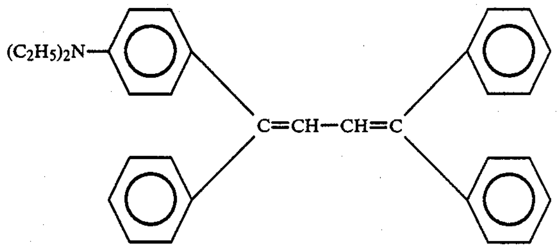

8. 1,1,4,4-tetraphenyl-1,3-butadiene derivative as in claim 6, wherein the compound of formula (I) is represented as follows:

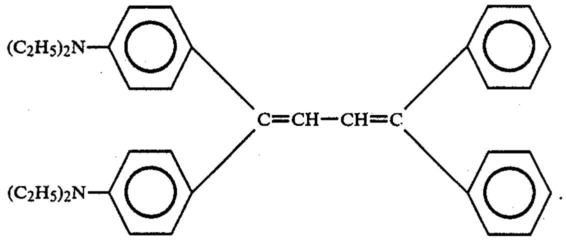

* * * * *